United States Patent
Wu et al.

(10) Patent No.: US 7,604,945 B2
(45) Date of Patent: Oct. 20, 2009

(54) SINGLE NUCLEOTIDE POLYMORPHISMS IN PROTEIN-TYROSINE PHOSPHATASE RECEPTOR-TYPE DELTA FOR THE DIAGNOSIS OF SUSCEPTIBILITY TO ASTHMA

(75) Inventors: Shih Hsin Wu, Taipei (TW); Ellson Ye-Shyon Chen, Taipei (TW)

(73) Assignee: Vita Genomics, Inc., Taipei (TW)

( * ) Notice: Subject to any disclaimer, the term of this patent is extended or adjusted under 35 U.S.C. 154(b) by 0 days.

(21) Appl. No.: 12/018,792

(22) Filed: Jan. 23, 2008

(65) Prior Publication Data

US 2008/0187932 A1  Aug. 7, 2008

Related U.S. Application Data

(62) Division of application No. 11/328,881, filed on Jan. 10, 2006, now abandoned.

(51) Int. Cl.
*C12Q 1/68* (2006.01)
(52) U.S. Cl. ......................................................... 435/6
(58) Field of Classification Search .................. None
See application file for complete search history.

(56) References Cited

U.S. PATENT DOCUMENTS

| | | | |
|---|---|---|---|
| 5,753,687 A | 5/1998 | Mjalli et al. | |
| 5,821,075 A | 10/1998 | Gonez et al. | |
| 5,858,701 A | 1/1999 | White et al. | |
| 6,525,083 B2 | 2/2003 | Acton, III et al. | |
| 6,569,879 B2 | 5/2003 | Liu et al. | |
| 6,645,997 B2 | 11/2003 | Sahoo et al. | |
| 6,713,508 B2 | 3/2004 | Sahoo et al. | |
| 2002/0042441 A1 | 4/2002 | Acton, III et al. | |
| 2002/0103242 A1 | 8/2002 | Sahoo et al. | |
| 2002/0150947 A1 | 10/2002 | Erlanson et al. | |
| 2002/0173663 A1 | 11/2002 | Liu et al. | |
| 2002/0177166 A1 | 11/2002 | Guthridge et al. | |
| 2002/0183518 A1 | 12/2002 | Mjalli et al. | |
| 2003/0064380 A1 | 4/2003 | Rao et al. | |
| 2003/0104404 A1 | 6/2003 | Wise | |
| 2003/0143606 A1 | 7/2003 | Olek et al. | |
| 2003/0144338 A1 | 7/2003 | Matsumoto et al. | |
| 2003/0170660 A1 | 9/2003 | Sondergaard et al. | |
| 2003/0194745 A1 | 10/2003 | McDowell et al. | |
| 2004/0029123 A1 | 2/2004 | Olek et al. | |
| 2004/0073037 A1 | 4/2004 | Jones et al. | |
| 2004/0092583 A1 | 5/2004 | Shanahan-Prendergast | |
| 2004/0092596 A1 | 5/2004 | Adams et al. | |

OTHER PUBLICATIONS

Burney, P.G.J., "*The European Community Respiratory Health Survey*", Eur Respir J. 1994, 954-960.
Lander, et al., "*Mapmaker: an interactive computer package for constructing primary genetic linkage maps of experimental and natural populations,*" Genomics 1:174-81 (1987).
Mustelin, et al., "*Protein tyrosine phosphatases and the immune response,*" Nature Rev. Immun. 5: 43-57(2005).
Pearce, N. et al., "*Comparison of asthma prevalence in the ISAAC and the ECRHS*", Eur Respir J. 2000; 16: 420-426.
van Huijsduijnen, et al., "*Selecting protein tyrosine phosphatases as drug targets*", Drug Discov. Today 7:1013-9 (2002).
Wang, Jiu-Yao, et al., "*Discovery of genetic difference between asthmatic children with high IgE level and normal IgE level by whole genome linkage disequilibrium mapping using 763 autosomal STR markers*", J Hum Genet (2005) 50:249-258.
Zhang, et al., "*Protein tyrosine phosphatases: prospects for therapeutics*", Chem. Biol. 5:416-423 (2001).
Zhao, Jing Hua, et al., "*Genecounting: haplotype analysis with missing genotypes*", Bioinformatics, vol. 18 No. 12 (2002), pp. 1694-1695.

*Primary Examiner*—Ruixiang Li
(74) *Attorney, Agent, or Firm*—Baker & McKenzie LLP

(57) ABSTRACT

A gene related to a susceptibility of infection and asthma—the Protein-Tyrosine Phosphatase Receptor-type Delta (PTPRD) gene—a method of detecting the asthma-associated gene, a method of predicting the occurrence of asthma, a method of identifying asthma-associated alleles in PTPRD gene, a method of screening PTPRD for drugs useful in the treatment of asthma, and antibodies specific for PTPRD variants and their use in diagnostic assays.

2 Claims, 1 Drawing Sheet

SINGLE NUCLEOTIDE POLYMORPHISMS IN PROTEIN-TYROSINE PHOSPHATASE RECEPTOR-TYPE DELTA FOR THE DIAGNOSIS OF SUSCEPTIBILITY TO ASTHMA

PRIOR RELATED APPLICATIONS

This application is a divisional application of U.S. Ser. No. 11/328,881, filed Jan. 10, 2006, now abandoned entitled "Single Nucleotide Polymorphisms in Protein-Tyrosine Phosphatase Receptor-Type Delta for the Diagnosis of Susceptibility to Infection and Asthma," which is incorporated herein in its entirety.

FEDERALLY SPONSORED RESEARCH STATEMENT

Not applicable.

REFERENCE TO A SEQUENCE LISTING

A "Sequence Listing" with sequences labeled SEQ ID NO: 1-75 is attached hereto. A compact disc containing a Computer Readable Form (CRF) labeled "SEQUENCE LISTING.txt" is incorporated by reference. The copy in CRF is identical to the compact disc copy of the "Sequence Listing" submitted herewith.

FIELD OF THE INVENTION

The present invention relates to the Protein-Tyrosine Phosphatase Receptor-type Delta (PTPRD) gene, which is related to the susceptibility of infection or asthma and various methods relating to same, including a method of detecting the asthma-associated gene, a method of predicting the occurrence of asthma, a method of identifying asthma-associated alleles in the PTPRD gene, a method of screening PTPRD for drugs useful in the treatment of asthma, and antibodies specific for PTPRD variants and their use in diagnostic assays.

BACKGROUND OF THE INVENTION

Asthma is a chronic airway inflammatory disease and affects nearly 155 million individuals worldwide. The population of asthma sufferers has been documented since 1970 and has increased continuously since then. A survey in 1994 by the U.S. Department of Health and Human Services identified over 12 million Americans suffering from asthma, almost 5 million of them under the age of 18. In addition, a patient's condition becomes more serious over time, resulting in increased hospitalization and possibly death.

Inheritance plays a strong role in some allergic diseases, including asthma. People whose relatives suffer from asthma are also at high risk of asthma. However, if allergic factors are reduced or removed early, it may possibly prevent the development of asthma. Many approaches have been proposed to determine if there are any allergen-specific IgE antibodies in the serum, but traditional IgE tests are limited to specific allergens and cannot detect asthma at such a low sensitivity. In addition, the preferred age for testing is above three years old and 6-8 c.c. of blood is required, thus limiting the usefulness of this test.

Another possible test for asthma would involve determining an individual's genetic predisposition for asthma. Genotypic diversity is assumed to underlie the heritable phenotypic differences observed as variations in drug response, susceptibility to disease, and other complex traits. Single Nucleotide Polymorphisms (SNPs) are the most common genetic variation and are of great value to biomedical research and in developing pharmacy products. SNPs make up 90% of all human genetic variations and occur every 100 to 300 bases along the human genome. Because SNPs do not change dramatically from generation to generation, following them during population studies is straightforward.

What is needed in the art is a method of identifying susceptibility to asthma and infection, which can be used to identify individuals with increased disease susceptibility even before disease is manifest, and thus allow those individuals to take measures to prevent disease.

SUMMARY OF THE INVENTION

To study the genetic disposition to asthma, a whole genome linkage disequilibrium mapping study was conducted by Wang, et al. on 190 allergic and non-allergic asthma children in Taiwan (25), the disclosure of which is incorporated herein in its entirety by reference. The linkage disequilibrium map identified populations and genomic regions with strong and weak associations with asthma. According to Wang, et al., the marker to marker synergetic analysis indicated six STR loci may play an important role in the incidence of asthma, one of which was near the PTPRD gene, and is described and claimed herein. The identification of a unique, common, and non-biased marker for asthma would provide a diagnostic and predictive tool for this debilitating disease, allow treatment or prevention before symptoms were manifested, and prevent mis-diagnosis once asthma symptoms were observed.

One aspect of the invention provides a method for predicting the occurrence of asthma by examining the polymorphisms of the PTPRD gene. The method has high prediction precision without restriction to the age, requires smaller and less invasive samples, and does not require that the patient to exhibit the physical symptoms of asthma. The invention is also useful for the determination of increased susceptibility to infection, particularly respiratory infections, which can be exacerbated by asthma.

Mucous fluids, blood samples, tissue, sinovial fluids, or other biological samples are taken from patients who would like to know their susceptibility to asthma. Nucleotide sequences, such as DNA, mRNA, or cDNA from the samples are subjected to genotyping. The genotyping may be conducted by a variety of techniques, including sequence-based methods, hybridization-based methods, restriction polymorphism-based methods, and combination methods, all of which are well known in the art. The method can also include amplification techniques, such as TAQMAN®, MC-PCR, or SNAPSHOT.™ By examining the genotypes of an asthma-linked gene, such as PTPRD, non-symptomatic individuals that are highly susceptible to asthma may be identified and monitored. Preventative measures may be employed to reduce and control the prevalence of asthma and related infections.

Furthermore, the invention provides a method of identifying additional alleles, such as SNPs, that may be associated with asthma. At the first step, one or more biological samples from a population of patients are obtained. The patients are evaluated for the clinical symptoms of asthma or infection. One or more alleles or SNPs in the PTPRD gene are selected for the biological samples to be tested or new alleles can be identified. Then, the SNPs that are associated with asthma or infection are identified by correlation with the two patient groups. Once an SNP associated with asthma is identified, additional mutations that occur in the same haplotype will also be associated with asthma. Hence, any SNP in a given asthma-associated haplotype can be employed in methods of the invention.

In order to achieve the above and other objectives of the invention, isolated nucleic acids that are complimentary to PTPRD genomic DNA are also provided. These nucleic acids usually comprise an SNP or other allele and correlate to an increased susceptibility of infection or asthma. Two specific nucleotides of the present invention are the SNPs at rs2279776 and rs767674, and specific oligonucleotides for detecting a C allele at rs2279776 and a G allele at rs767674 are also disclosed.

A screening method for an asthma treatment drug is further provided. A PTPRD protein or polymorphic variant thereof is contacted with a test agent. Then, the activity of PTPRD protein or polymorphic variant thereof is measured. In this embodiment, a decrease in PTPRD activity is used to identify an agent for treating asthma. The polymorphic variant of PTPRD may be selected from the group consisting of I130M, E447Q, D1078E, or V1486D (see Table V), but other alleles will also suffice.

Antibodies for diagnosing asthma are also provided. The antibodies include those that bind specifically to an asthma causing PTPRD epitope, such as I130M, E447Q, D1078E, or V1486D. Antibodies also include those that bind to both wild type and variant PTPRD, and those that bind only to wild type PTPRD.

In still another aspect of the invention, methods for the detection, diagnosis, and screening of disorders related to the polymorphisms of PTPRD gene are provided. The role of PTPRD in disease is not yet understood, but it is a receptor-type protein-tyrosine phosphatase expressed in the specialized regions of the brain and PTPRD-deficient mice are semi-lethal due to insufficient food intake and have learning impairments. This suggests an important role in brain development and learning, and possibly in hunger regulation, and indicates that the invention has broader application that herein exemplified.

DETAILED DESCRIPTION OF THE INVENTION

Figure 1:
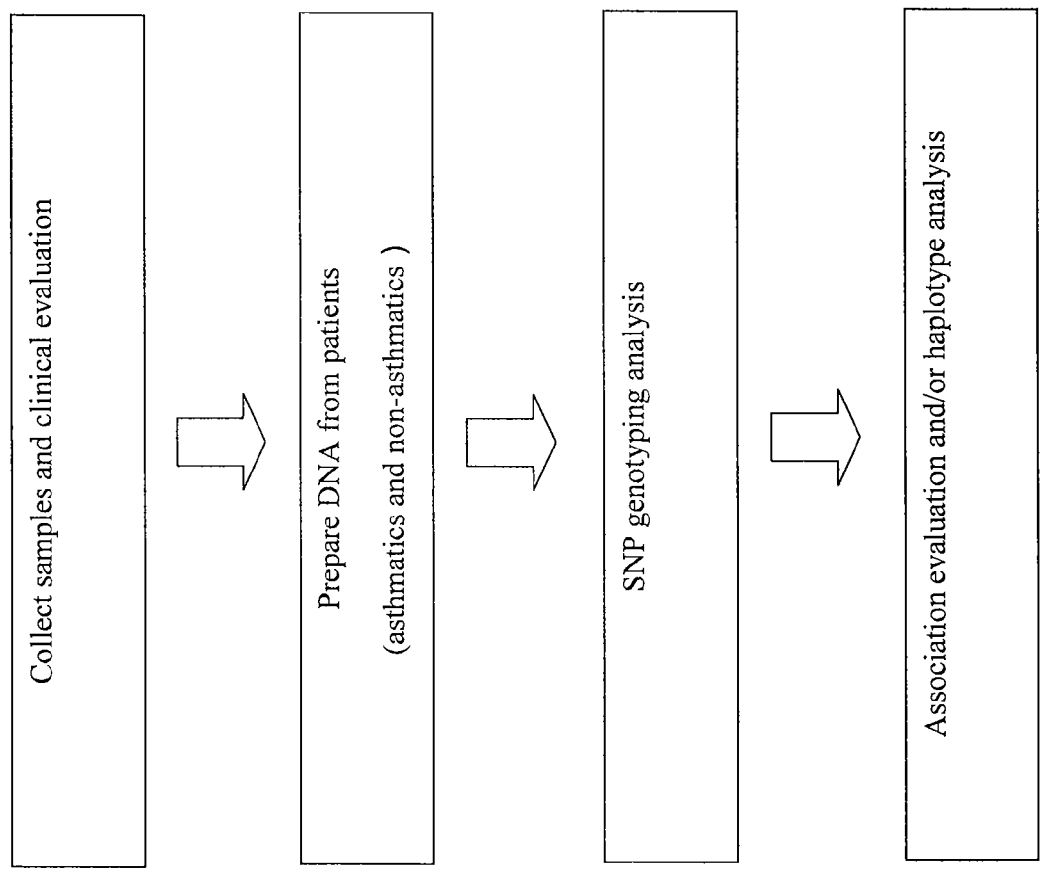
FIG. 1 is a flow chart for the detection of PTPRD gene loci related to susceptibility to infection or asthma.

As used herein "recombinant" is relating to, derived from, or containing genetically engineered material.

"Single Nucleotide Polymorphism" or "SNP" refers to single-base pair variations within the genetic code of the individuals of a population. SNPs and other alleles can be identified de novo through population analysis or can be selected from numerous databases including the National Center for Biotechnology Information (NCBI) SNP database (dbSNP), the SNP Consortium (TSC) database, Human Genome Variation Database (HGVbase), and the ABI database (Applied Biosystems, Foster City, Calif.).

"Protein-Tyrosine Phosphatase Receptor-type Delta" or "PTPRD" variants of which are found at GenBank Acc. # NP_002830, NP_569075, NP_569076, and NP_569077. The genomic DNA which encodes PTPRD can be found at GenBank Acc. # AL137125, AL356584, AL445926, AL583805, and AL590397. The PTPRD gene is located on chromosome 9 (NC_000009) with about 1833 SNPs identified to date.

"Molecular beacon," "marker," and "probe" are used interchangeably to reflect various labels that can be used to bind or mark specific nucleic acid sequences.

As used herein the term "test agent" refers to a candidate drug that is being tested for efficacy against a given target protein.

According to one embodiment of the present invention, a gene for asthma prediction may be found by genotyping analysis, as illustrated in FIG. 1. A genetic contribution to the pathogenesis of asthma has long been inferred from the increased prevalence of asthma in families. The D9S286 locus is one of the six STR loci identified by Wang, et al. (25). Searching DNA databases, the D9S286 locus was located on chromosome 9 p-arm at a physical distance of 8.04 MB from the p-terminal of the PTPRD gene. The PTPRD gene at NC_000009 spans 416.68 kb and has 35 exons.

Protein tyrosine phosphatases (PTPs) form a large family of enzymes that serve as key regulatory components in signal transduction pathways. The cells of the immune system express at least half of the 107 protein tyrosine phosphatase (PTP) genes in the human genome. Moreover, PTPs have a crucial role in both the maintenance of a resting lymphocyte phenotype and the reversion of activated lymphocyte to a resting state during the termination of an immune response.

Due to proximity to the D9S286 locus and possible role in immune response, the protein translated from PTPRD gene may also play an important role in the diagnosis and treatment of asthma. Of the many SNPs associated with the PTPRD gene, 72 SNPs (SEQ ID NO: 1-68) are shown in Table 1. Using association evaluation, polymorphisms in the PTPRD gene were correlated with a susceptibility to asthma. A patient having at least one C allele at rs2279776 had an increased risk of asthma, and a patient homozygous for a C allele at rs2279776 had a greater risk of asthma. Likewise, a patient heterozygous for a G allele at rs767674 had an increased risk of asthma and a patient homozygous for a G allele at rs767674 had a greater risk of suffering asthma. By examining these two loci of PTPRD gene, the susceptibility to asthma may be evaluated as low, medium, and high risk of asthma.

The Hardy-Weinberg equilibrium (HWE) test, linkage disequilibrium (LD) test, in-silico haplotype reconstruction module, and SNP (or haplotype)-phenotype association module are some known analysis tools which help associate SNPs (or haplotypes) with phenotypes. Chi-square test and SAS are used here, for example. There are many analysis programs available including ARLEQUIN® (Schneider, et al., Genetics and Biometry Laboratory, Geneva, Switzerland); CIA® (Gardner, British Medical Journal, 1989); MAPMAKER™ (Lander, et al. Genomics 1:174-181); GENECOUNTING™ (Zhou, et al., Bioinformatics 2002, 18:1694-1695); HAPLO™ (Hawley and Kidd, J Hered 1995, 86:409-411); and SNPHAP™ (Clayton, Addenbrooke's Hospital, Cambridge, CB2 2XY).

The genotyping analyses of PTPRD SNP allele frequency and genotype frequency allowed association with the asthmatic phenotype. Allele frequency and genotype frequency differences were calculated by using $\chi^2$ test to obtain alleles with significantly different frequency between asthma-infected and non-asthma-infected DNAs. Moreover, SNPs with a p value <0.05/72 (0.0007, Bonferroni correction) in allele by using $\chi^2$ test were selected to limit the number of SNPs analyzed. Two SNPs, rs2279776 and rs767674, that correlate to a susceptibility to infection or asthma were identified.

The method comprises sampling genomic DNA, mRNA, or cDNA extracted from tissue, blood, mucous and sinovial fluids, and other patient samples and detecting polymorphisms or other alleles associated with asthma. Patient samples are analyzed to identify the genotypes of loci rs2279776 and rs767674, or those SNPs associated therewith by virtue of being in the same haplotype. The susceptibility to asthma is then assessed for each patient as low, medium, or high based on the genotype at rs2279776 and rs767674.

EXAMPLE 1

Study Population

A population of 1000 asthmatic children between 1 to 12 years old was analyzed. "Asthma" was diagnosed through the three following conditions: (1) History of wheezing and shortness of breath with or without respiratory infections; (2) Chronic cough for more than one month and/or one or more wheezing episodes in the presence of a physician; and (3) Bronchodilator test with a positive increase of 15% for FEV1.

Other evaluations included skin prick tests for responsiveness to 6 common aeroallergens, a differential blood count (including total eosinophil count), and measures of total serum IgE, as well as IgE specific to house dust and mixed pollens using UNICAP™ system (PHARMACIA DIAGNOSTIC™, Sweden). A positive skin test was defined as the presence of ≧1 reaction with a wheal diameter ≧5 mm. Total serum IgE was measured by solid-phase immunoassay (PHARMACIA™ IgE EIA).

The study protocol was approved by the Ethical and Clinical Trial Committee of National Chen-Kung University Hospital. All participants or their guardians were well informed and signed consent forms and answered a modified British Medical Society respiratory questionnaire that is identical to the European Community Respiratory Health Survey (ERCHS). Questions were similar to those used in the International Study of Asthma and Allergies in Childhood (ISAAC) (Burney, et al., 1994; Pearce, et al., 2000), as well as additional questions pertinent to the diagnosis and assessment of asthma. Pulmonary function was tested using standard methods that included spirometry before and after the administration of two puffs of inhaled salbutamol (200 ug/puff).

EXAMPLE 2

Sample Preparation

Genomic DNA was extracted from blood samples for 1000 children using QIAAMP™ DNA Blood kit (QIAGEN) by following the manufacture's instructions. The extracted genomic DNA was confirmed by agarose gel electrophoresis analysis, quantified by spectrophotometer, and stored at −80° C. until use.

All SNP genotypes were analyzed using the TAQMAN® SNP genotyping assays (APPLIED BIOSCIENCES™) and 1 to 20 ng of purified genomic DNA. 2×TAQMAN® Universal PCR Master Mix, without AMPERASE® UNG, and 20×SNP Genotyping Assay Mix were used, wherein the SNP Genotyping Assay Mix contained: (1) sequence-specific forward and reverse primers to amplify the SNP of interest (See Table IV for primer sequences); and (2) two TAQMAN® MGB probes labeled with VIC™ dye for Allele 1 and FAM™ dye for Allele 2. The reaction mixture was PCR amplified and an endpoint measurement was used to detect each allele.

Specifically, reaction mix was prepared by gently resuspending 2×TAQMAN® Universal PCR Master Mix. The 20×SNP Genotyping Assay Mix was vortexed and centrifuged briefly. 5 µl of 2×TAQMAN® Universal PCR Master Mix and 0.5 µl of 20×SNP Genotyping Assay Mix were pipetted into a sterile tube. Finally, the tube was inverted to mix and centrifuged briefly to collect the contents.

The reaction plate was prepared by diluting 1 to 20 ng of each purified genomic DNA sample into DNase-free water to a volume of 4.5 µl. Control or sample was pipetted into each well of the 96-well or 384-well optical reaction plate and reaction mix added to a total volume of 10 µl. The plate was centrifuged briefly to collect the contents and to eliminate air bubbles. Finally, the plate was covered with an optical adhesive cover.

Amplification and the fluorescence signal detection were carried on ABI prism 7900 Real-Time PCR System with following thermal reactions: one cycle of warming up at 95° C. for 10 minutes, 40 cycles of denaturing at 92° C. for 15 seconds and annealing/extending at 60° C. for 1 minute.

EXAMPLE 3

Alternate Sample Preparation

In another embodiment of the invention, the genotyping of a patients PTPRD gene was conducted by SNAPSHOT™, wherein each reaction contained 2.5 µl of 10×Reaction Buffer, 0.5 µl of 10 mM dNTPs, 2.5 µl 25 mM $MgCl_2$, 16.375 µl sterile deionized water, 1.0 µl primer pair (5 µM each primer), 1 µl genomic DNA (10 ng) and 0.125 µl of 5 U AmpliTaq Gold® for a total reaction volume of 25 µl/well. Amplification and the fluorescence signal detection were performed using an ABI prism 7900 Real-Time PCR System™ with following conditions: One cycle at 94° C. for 12 minutes, 35 cycles of melting at 94° C. for 30 seconds, annealing at 58° C. for 45 seconds, extending 72° C. 1 minute, 1 cycle at 72° C. for 10 minutes and hold on 4° C.

The amplification was followed by Exo-SAP™ reaction whereby Shrimp Alkaline Phosphatase (SAP) dephosphorylates residual deoxynucleotides preventing them from participating in sequencing reactions, and Exonuclease I degrades excess ssDNA (primers) from sample. The Exo-SAP mix included 0.2 µl of exonuclease I (10 U/µl), 0.2 µl of SAP (2 U/µl)–0.6 µl of SAP (1 U/µl), 0.2 µl of sterile deionized water, and 5 µl of PRC product (total 7 µl/well). The Exo-SAP program is one cycle at 37° C. for 45 minutes, following by 94° C. for 15 minutes and finally a hold at 4° C.

Then, the SNaPshot™ reaction was conducted. The total volume of SNaPshot™ components was 10 µl/well including 1.25 µl of SNaPshot™ reaction mix, 2 µl of 1 µM probe, 1.5 µl of 3×sequencing buffer, 2.25 µl of sterile deionized water, and 3 µl of diluted Exo-SAP treated product (total 0.01-0.04 pmol). The SNaPshot™ program was one cycle at 96° C. for 5 minutes, 25 cycles of melting at 94° C. for 10 seconds, annealing at 50° C. for 5 seconds, extending 60° C. 30 seconds, 1 cycle at 60° C. for 5 minutes, and finally a hold at 4° C.

In order to remove excess labeled ddNTPs, the post-extension reaction was carried out, wherein the components were 1 µl of 1 U SAP and 10 µl of SnapShot® product and the program was one cycle at 37° C. for 1 hour, followed by one cycle at 75° C. for 15 minutes and a hold at 4° C.

Reaction components were analyzed on a 3700 DNA analyzer, including 9 µl of Hi-Di formamide, 0.15 µl of GeneScan LIZ120, and 0.85 µl of SAP treat SNaPshot™ product. The products were denatured at 95° C. for 5 minutes and quenched at 4° C. Finally, the fluorescence signal was detected using the SNP_POP5_CT49RT60 module.

EXAMPLE 4

Asthma Association

To determine the relationship between asthma and PTPRD SNPs, association analyses including allele frequency and genotype frequency were performed by $\chi^2$ tests or Fisher's exact tests using standard software packages. All statistical analyses were performed by SAS® (SAS INSTITUTE INC.™, Cary, N.C.).

$\chi^2$ tests identified the significantly higher frequencies of the rs2279776 and rs767674 polymorphisms in asthmatic patients compared to normal subjects, wherein the frequency of the homozygous form of C allele in 100 asthmatic subjects and 53 normals at rs2279776, and the frequency of the homozygous form of G allele in 152 asthmatic subjects and 96 normals at rs767674 were determined, as shown in Table II and Table III ($\chi^2$, p<0.05). Patients with a homozygous C allele at rs2279776 or a homozygous G allele at rs767674 of PTPRD gene have higher risk of suffering asthma as compared with patients having at least one G allele at rs2279776 or A allele at rs767674, respectively.

EXAMPLE 5

Patient Diagnosis

In another aspect of the invention, a method of screening potential asthmatics by identifying the asthma-causative gene among those currently non-asthmatics is disclosed.

Mucous membranes, blood samples, or any biological samples are taken from patients who would like to determine if they have a susceptibility to asthma. This may be particularly useful in those patients with a family history of asthma. Samples are subjected to genotyping by SNAPSHOT™ or any other method, whereby the sample is genotyped at the PTPRD gene, preferably at loci rs2279776 and rs767674 or an allele in the same haplotype. Those with a C allele at rs2279776 or G allele at rs767674 are regarded as potential asthmatics, and those with a homozygous C allele at rs2279776 or a homozygous G allele at rs767674 have an even higher susceptibility for asthma.

EXAMPLE 6

Asthma Drug Screening

Now that a protein that contributes to asthma has been identified, it will be possible to use the PTPRD protein as a target in drug screening for potential asthma drugs. In such method, the wild type or variant PTPRD is tested against a drug library and those compounds that change PTPRD activity are identified as lead compounds for use in asthma treatments.

EXAMPLE 7

Antibody-Based Diagnostics

The PTPRD gene also has asthma-associated alleles that manifest as changes in the primary amino acid sequence. Such protein variations can be used in antibody-based testing methods, whereby antibodies can be generated and are specific to these alleles, as shown in Table V. In addition, antibodies that are specific to the wild type PTPRD or antibodies that will bind to both wild type and variant PTPRD can be used as a control to indicate whether a patient is homozygous (only one signal) or heterozygous (two signals) at the loci in question.

Realizations in accordance with the present invention have been described in the context of particular embodiments. These embodiments are meant to be illustrative and not limiting. Many variations, modifications, additions, and improvements are possible. Accordingly, plural instances may be provided for components described herein as a single instance. Additionally, structures and functionality presented as discrete components in the exemplary configurations may be implemented as a combined structure or component. These and other variations, modifications, additions, and improvements may fall within the scope of the invention as defined in the claims that follow.

TABLE I

SNP Sequences near or within the PTPRD genomic DNA.

| SEQ ID | ABI # | NCBI #: | SNP | Sequence |
|---|---|---|---|---|
| 1. | hCV8781206 | rs3843579 | C/G] | TGTGTGTGTCATGATTCTAGATTGTNCTAACCTATCCAGCAAGTTCAAAAC |
| 2. | hCV8781198 | rs996924 | A/G | CCCAGACAAGTGTTTTCCAAGTAGTNTCAAACCATTACCACCAATTGAACA |
| 3. | hCV11260659 | rs12001948 | C/G | AATTCATAGCTCTTGTGCACTTAAGNAGGAAAGCAATGGGAAGTTCAGATA |
| 4. | hCV1430259 | rs10739155 | A/C | AAGGATGCTAGAAGGGACTTTAAACNTCAGCTAAGATAACTGAAGTCCAGA |
| 5. | hCV1430252 | rs10815823 | C/G | TCCTGACTGATGTTATTTGGGGATGNAGATAAACAGGAAGATGACACCAAG |
| 6. | | rs3780336 | A/C | GCTTTCATTCAAACATAACATCTGGNAGCTCAACCTTGGGGATGCACTTGG |
| 7. | | rs1500318 | C/T | ACTCTGTAATCATTTTGAAACTTCANGCTATAAAAGACTTCAGATGTAGAA |
| 8. | | rs1500322 | C/G | GGCCAGAATATAGCAATGTGGTATGNAATCAGAAAGGAAGGAGTGGCTCAT |
| 9. | | rs1039336 | A/G | GACAAATATTTGCGCAGGAAGACAANATTCTTAGGTGAGAAGCATTATATT |
| 10. | | rs1566447 | C/T] | AAATGGCTGAGTGATAATGGAAGATNTATTTCATTCTTCACTGTTGCCATT |
| 11. | | rs989815 | C/G | TTCTAATTCACAGCAGCATTTACAANACGCACACATATTTTCTTCATGTAC |

TABLE I-continued

SNP Sequences near or within the PTPRD genomic DNA.

| SEQ ID | ABI # | NCBI #: | SNP | Sequence |
|---|---|---|---|---|
| 12. | | rs2279776 | C/G | CAATATAGGCATTTTGCTTCCTATANCCATCTATGTAGTTGGCATTCACAT |
| 13. | | rs1500331 | C/G | CATTTCAGGTAAGTTCTCTCTCACANATCCTCTGCAAATGTGGAGATAAGA |
| 14. | | rs1392524 | A/C | TCCATTTATCAAGCACCAGTGTTTTNTTTTGCATTACAGAGTACTTCAAAT |
| 15. | | rs1021720 | A/C | CTTTTCCACCCATGCTAAGTGACTTNAGACACTGTCACATCCTGCACCGGT |
| 16. | | rs1875239 | C/T | GAAGAAGCCCAACTTAAGAAACACANCTACACATCACTATCCTTTATTTCA |
| 17. | hCV7580286 | rs3903826 | C/T | GCAGCTTTTGACTAAACCTTTCTAANGCTAACAACAGATCTTCAACTCAAA |
| 18. | hCV3046499 | rs4742500 | C/G | GTCAGTTAGTAGGAGAGAAAGCAAGNCACAGACATGCAGACAATGGAGGG |
| 19. | | rs1535677 | C/G | ACCCTCCATCCTTGTCACCCTTTACNTTCCCCTAATTGCTTTCATAGAGCT |
| 20. | hCV1634600 | rs10977105 | C/T | AAAGAATGACATGCACCACGACTCANTGACGATAATCACTGACGGCACAAT |
| 21. | hCV1634601 | rs10815874 | C/T | TGGTCTGGAAGTATTATATTGGAAGNTTATTAAAGAAAAATTCAAGCAGAC |
| 22. | hCV1634606 | rs7853571 | A/C | TGAGGAATCTGATCCCATACCCCGTNCACTCTCATTTAGCACATTTCACAT |
| 23. | hCV1634612 | rs10977113 | G/T | TTTTTAAGATGCCAAGTTATCCTAANGCCTAGGATAATCGGGACCAGGTAA |
| 24. | | rs1323590 | A/G | TAAAGGTCAGCCTCACCATACACCTNGGTACATATGTGGTACAAATATCTA |
| 25. | | rs1407972 | C/T | TTAAAACTTTTATCTCTGGCTCTCTNAATTTTGAATTAAACCAGTCCCATC |
| 26. | | rs1359119 | A/G | TTTTACAAGGAGCAAGGGGCAAAATNTTAAGGCCAACAAAGATTAGACAGG |
| 27. | | rs2296100 | A/G/T | TTAGCCCACATAAATACCTAGTAGTNCTGTTGTTTATACAAACCTAAAATG |
| 28. | | rs767674 | A/G | TGCCAACCACGGCAAGTGACACAGCNTGGCACGGAGCTTCTTGTAATACCT |
| 29. | | rs767675 | A/G | ATACCTGACCGTGTTACATTAACCANTCTAGAAAACAGGAGTAGTAACCTT |
| 30. | | rs2296102 | G/T | TTTGTCATTTATGAGCATGTTCTTANTAACTGATGTTTCACTTTATAATAT |
| 31. | hCV11260427 | rs6477311 | A/T | TACATAGAGGTATGTTCCTAAAAAGNTATTTGAAGAGTGATTCGGGCAGAG |
| 32. | hCV1634689 | rs10124277 | C/T | TTGTTTTAGGACAGAAGAAAGTAGANTCCATCAGCAAAATTGCAGTTTAGA |
| 33. | | rs1538192 | C/G | AACTCCTGACTCAAACCAAACCGGANTACAGTATGGTCAAGAATTAGAAAC |
| 34. | | rs3763653 | C/T | AACCTCCAGGAACTCCTGTAGTGACNGAGAGCACAGCTACAAGCATCACAC |
| 35. | hCV1634718 | rs7039690 | A/G | ATATAACATTATTTCACGATTGTAANTGTTGACAATGTGTACCTTTGTTCT |
| 36. | | rs1407970 | C/G | GTCCCACCATAATGGTCGACCATGTNTAAAATTCCTAGTTCTGTCTGGTTA |
| 37. | | rs3818346 | C/T | CATTAGTCACTTGGCTTGAGTGTACNCGATCCTCAAAGCATAATCCATTG |
| 38. | hCV1634734 | rs7046918 | A/G | TAATGGCTAAAAAGCCCAGGAGTGNACCACTCAGTTTTTTGTTGAGGCA |
| 39. | hCV1634737 | rs10815909 | G/T | TTTTGTGATTCATAATCAAATAAACNCATTGAGAAAAAAAGAAGTACCTT |
| 40. | hCV1634743 | rs13298042 | A/T | CAGTCATGTCTTCCCTTGGGAAGCANTGTCATGTATTTGAGGCACTCATGA |
| 41. | hCV1634752 | rs7855892 | C/T | CCCTTCCTTAAGTGACTTTAACCTCNGTAGGCATTGGGCCCCATGACCCAT |
| 42. | hCV1634763 | rs13294631 | C/T | ACGGAAACAAATGTAACTGATACATNTGAAGCAAGAGGAGATTGAAGATGA |
| 43. | hCV11260346 | rs10511500 | A/C | ACGCTTATCAAAAAGAACTGGGGTANGTTATTCATCAAAGTTTTATCATTA |
| 44. | hCV1824069 | rs10815918 | C/T | CTTTCCATTTTAGTTTCTTTATTTGNAAAATTAAGAGTCAGAATATAGCCT |
| 45. | hCV1824085 | rs13293506 | A/G | AAAAGAAATCCCTATCTATAAATACNATGTCTTTTCTGGTCACATCTTGCA |
| 46. | hCV1824088 | rs12000186 | C/T | CAAAGATTTCTGGGGTTATGAACGTNGGTTTTTGCAATGTTCACGAGGTTC |
| 47. | hCV2755916 | rs11788439 | A/G | TAAAACCTCATGTTCCTATATTACTNTGCTGTTAACAGAAACAGCTTGCAG |
| 48. | hCV2755908 | rs12685150 | C/G | ATGTATCAAGCACCTAGTCATTGTGNCAGATTGGGGAATCTAGGTACAAAA |

TABLE I-continued

SNP Sequences near or within the PTPRD genomic DNA.

| SEQ ID | ABI # | NCBI #: | SNP | Sequence |
|---|---|---|---|---|
| 49. | | rs2175595 | A/T | CATATGGTATTCCTAATAAAGAGATNAGATAGGAAGAACGAGAGGTATTTC |
| 50. | | rs1415723 | A/T | TTAAAGTTTCGTAAGCTTTAGACTTNATAATATCTAGGTCCGCTGCTGGGA |
| 51. | hCV2755889 | rs7041298 | C/T | CTGACCACAACTTCTCATCTATCAANTGCACACTGGTTAAGTTGGCAAGAT |
| 52. | | rs907625 | C/T | CCTCAGTTTCCCCAAATATTAACCANATTTGGTTGAAATCTTTCTGAAATA |
| 53. | hCV8781326 | rs1025547 | G/T | TTAAATGCAATCTCTTGAGTCCCATNGTTTTATCACAGAAAGGTACACTTC |
| 54. | hCV11837290 | rs10815923 | C/T | AGAGCTCAGGAATATGGCATCTTATNTGTTTTACTCCCCCTCCACTATGGA |
| 55. | hCV2755884 | rs10977243 | A/G | CACAAGTTTTCATTCAAACTAAATTNCCAGTTAAGGCTATTATCTCCTCAT |
| 56. | | rs2137346 | G/T | TTAATGCATATTTGCATGAAACATTNTATTCTTTACCAAAGCATTTTATTT |
| 57. | | rs1434265 | A/G | TAATGCCTATATTTGGCCATGAGTTNCTAGGATACAGTTTCTTTCCATGTT |
| 58. | | rs1368982 | C/T | TTTCTGAGCAATCAAATAGAAATCCNATATAGGGTAAGGAGTCAATAACAT |
| 59. | hCV2755866 | rs10815925 | C/G | ATGCACTGAAAATACAGCAATTTTANGGTAGTTCCAGCAGGGGATAATTT |
| 60. | | rs906636 | A/G | TTGATAAACATAGATGTCTAATGGCNCTTAACCTTTAAAATGTATGCAGAA |
| 61. | | rs1473822 | C/T | GGTTAAAGAATTGGTTCTAAAATGGNATCTCCATCCAATCACAGGACCTTT |
| 62. | hCV8781341 | rs1004489 | A/T | CAAAATTTCTTTATTTTTGTGGATCNTTCCGTGTTTAGAAAAATGCACAAT |
| 63. | | rs1434249 | C/G | TTGGCATGAAGAAGCAAGTGGTACANTGAAAACTTCTTGAATCCAGAAGC |
| 64. | hCV2755837 | rs6477331 | G/T | TTTCCTCCTACTCAGCTGAAGTGCANAAGAAGACCAAATTTTTTCAAATGA |
| 65. | | rs2033554 | G/T | GCCAGTAGAAACTGGCAATGAAACGNTTAAAATACAAGTCTATTCAACATG |
| 66. | | rs2033555 | C/G | TCCTTTCATCCAAAAAGACACTGTANAAGTGAGAAACAGATCTTTGTCGCA |
| 67. | hCV1058592 | rs3887368 | C/T | GTTTCTTAAACTGTCTAACAGATAANAGGCTTGATCTTTATTGTCTTCCTC |
| 68. | | rs723145 | C/T | GGAAAAAATAAAACAGTTGTCCTGTNCCTTCTTACCTCCGCTTGATTTAAG |
| | hCV249839 | ss43800463 | G/T | not available |
| | hCV8079848 | ss43852382 | A/T | not available |
| | hCV1634758 | ss43746783 | G/T | not available |
| | hCV1634732 | ss43760597 | A/G | not available |

TABLE II

Asthma associated with rs2279776 CC genotype.

| rs2279776 | CC | CG | GG |
|---|---|---|---|
| Asthma | 100 | 217 | 154 |
| Non-Asthma | 53 | 255 | 214 |

TABLE III

Asthma associated with rs767674 GG genotype.

| rs767674 | AA | AG | GG |
|---|---|---|---|
| Asthma | 108 | 211 | 152 |
| Non-Asthma | 190 | 236 | 96 |

TABLE IV

Primer Sequences

| SEQ ID NO. | Primer Sequence | Name |
|---|---|---|
| 69. | GATCCCAGGAAGTGACTATGTG | forward primer for TAQMAN ® assay |
| 70. | GGAGAGATCCCTGTGTTGCAAT | reverse primer for TAQMAN ® assay |

TABLE IV-continued

Primer Sequences

| SEQ ID NO. | Primer Sequence | Name |
|---|---|---|
| 71. | CCAACTACATAGATGGGTATAGGAAGCAAAATGC | MGB Probe-VIC ™ for allele 1 |
| 72. | CCAACTACATAGATGGCTATAGGAAGCAAAATGC | MGB-probe-FAM ™ for allele 2 |
| 73. | GTGCTCACCTGGTTGAATAACA | forward primer for SNAPSHOT ® assay |
| 74. | ATGCAACATAGGGACTCTGAGG | reverse primer for SNAPSHOT ® assay |
| 75. | ATCGATCGATCGATTGTGAATGCCAACTACATAGATGG | SNAPSHOT ® probe |

TABLE V

Polymorphic PTPRD Proteins

| SNP | Polymorphism |
|---|---|
| rs1061345 | I130M |
| rs10977171 | E447Q |
| rs7869444 | D1078E |
| rs2133788 | V1486D |

All citations are hereby expressly incorporated by reference and are listed here for convenience:

1. U.S. Pat. No. 6,713,508, Sahoo, Soumya P., et al., (2001).
2. U.S. Pat. No. 6,645,997, Sahoo, et al., (2003).
3. U.S. Pat. No. 6,569,879, Liu, et al., (2003).
4. U.S. Pat. No. 6,525,083, Acton, III, et al., (2003).
5. U.S. Pat. No. 5,858,701, White, et al., (1999).
6. U.S. Pat. No. 5,753,687, Mjalli, et al., (1998).
7. US 20040092596, Adams, Alan D., et al., (2004).
8. US 20040092583, Shanahan-Prendergast, Elizabeth, (2004).
9. US 20040073037, Jones, A. Brian, et al., (2004).
10. US 20030194745, McDowell, Robert S., et al., (2003).
11. US 20030144338, Matsumoto, Takahiro, et al., (2003).
12. US 20030143606, Olek, Alexander, et al., (2003).
13. US 20030064380, Rao, Anjana, et al., (2003).
14. US 20020183518, Mjalli, Adnan M. M., et al., (2002).
15. US 20020177166, Guthridge, Mark Andrew, et al., (2002).
16. US 20020173663, Liu, Kun, et al., (2002).
17. US 20020150947, Erlanson, Daniel A., et al., (2002).
18. US 20020103242, Sahoo, Soumya P., et al., (2002).
19. US 20020042441, Acton, John J. III, et al., (2002).
20. US 20040029123, Olek, Alexander, et al., (2004).
21. US 20030170660, Sondergaard, Helle Bach, et al., (2003).
22. US 20030143606, Olek, Alexander, et al., (2003).
23. US 20030104404, Wise, Carol A., (2003).
24. U.S. Pat. No. 5,821,075, Gonez, et al., (1998).
25. Huihsduijnen, et al., DDT 7:1013-1019 (2002).
26. Lander, et al., *Genomics* 1:174-181 (1987).
27. Mustelin, et al., Nature Rev. Immun.: 43-57 (2005).
28. Wang, et al., J. Hum. Genet. 50:249-258 (2005).
29. Zhang, et al., Chem. Biol. 5:416-423 (2001).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07604945B2). An electronic copy of the "Sequence Listing" will also be available from the USPTO upon request and payment of the fee set forth in 37 CFR 1.19(b)(3).

What is claimed is:

1. A method of determining susceptibility to asthma, comprising obtaining a biological sample from a patient and detecting at least one allele within the PTPRD gene, wherein said allele is a C at the rs2279776 loci or a G at the rs767674 loci, thereby indicating that the patient is susceptible to asthma.

2. The method of claim 1, wherein detecting both a C at the rs2279776 loci and a G at the rs767674 loci indicates that the patient has higher susceptibility to asthma than if only a single allele is detected.

* * * * *